United States Patent [19]

Geisberger

[11] Patent Number: 5,434,286
[45] Date of Patent: Jul. 18, 1995

[54] PROCESS FOR THE PREPARATION OF DIMETHYLCHLOROSILANE

[75] Inventor: Gilbert Geisberger, Altötting, Germany

[73] Assignee: Wacker-Chemie GmbH, Munich, Germany

[21] Appl. No.: 158,558

[22] Filed: Nov. 29, 1993

[30] Foreign Application Priority Data

Dec. 3, 1992 [DE] Germany .................. 42 40 730.3

[51] Int. Cl.$^6$ .............................................. C07P 7/08
[52] U.S. Cl. .................................................. 556/469
[58] Field of Search ...................................... 556/469

[56] References Cited

U.S. PATENT DOCUMENTS

| | | |
|---|---|---|
| 3,399,222 | 8/1968 | Weyenberg . |
| 4,410,669 | 10/1983 | Panster et al. . |
| 4,613,491 | 9/1986 | Jung et al. . |
| 4,870,200 | 9/1989 | Ottlinger et al. . |
| 5,094,831 | 3/1992 | Klockner et al. . |
| 5,130,396 | 7/1992 | Panster et al. . |
| 5,252,768 | 10/1993 | Geisberger et al. . |

FOREIGN PATENT DOCUMENTS

| | | |
|---|---|---|
| 0138670 | 4/1985 | European Pat. Off. . |
| 0206621 | 12/1986 | European Pat. Off. . |
| 0286074 | 10/1988 | European Pat. Off. . |
| 0560363 | 9/1993 | European Pat. Off. . |
| 1457139 | 9/1966 | France . |
| 4208152 | 9/1993 | Germany . |

OTHER PUBLICATIONS

Walter Noll, Chemie und Technologie der Silicone, (Chemistry and Technology of the Silicones), Verlag Chemie Weinheim, 2nd Edition, pp. 76–77 (English version pp. 87–89), Aug. 1968.
E. L. Zicky, J. Organometal., Chem. 4, 411–412 (Feb. 1965).
Chemical Abstracts, vol. 110, Jun. 1989, p. 492, 102628t.

*Primary Examiner*—Paul F. Shaver
*Attorney, Agent, or Firm*—Martin Connaughton

[57] ABSTRACT

A process is described for the preparation of dimethylchlorosilane by redistribution of dimethyldichlorosilane with methylchlorosilane and/or methylsilane in the presence of a catalyst. The catalyst may be shapeless or in the form of spheres and is a polymeric, optionally crosslinked organosiloxane-ammonium compound having a silica-type backbone.

6 Claims, 1 Drawing Sheet

PROCESS FOR THE PREPARATION OF DIMETHYLCHLOROSILANE

FIELD OF THE INVENTION

The invention relates to a process for the preparation of dimethylchlorosilane by redistribution of dimethyldichlorosilane with methylchlorosilane and/or methylsilane in the presence of a catalyst.

BACKGROUND OF INVENTION

In so-called direct synthesis, a process in which silicon powder is reacted with methyl chloride in the presence of a copper catalyst, further silanes, such as dimethylchlorosilane, but only in low yields, are also obtained in addition to the main product dimethyldichlorosilane.

According to U.S. Pat. No. 3,399,222, for redistribution of dimethyldichlorosilane with methyldichlorosilane in the presence of quaternary ammonium salts, the following equilibrium lies on the lefthand side:

$$(CH_3)_2SiCl_2 + CH_3HSiCl_2 \rightleftharpoons (CH_3)_2HSiCl + CH_3SiCl_3$$

U.S. Pat. No. 4,870,200 describes the disproportionation of methyldichlorosilane to give methylchlorosilane and/or methylsilane in the presence of a catalyst comprising a support which is insoluble in the reaction medium and on which tertiary amine groups or quaternary ammonium groups are covalently bonded.

U.S. Pat. No. 5,252,768 describes a process for the preparation of dimethylchlorosilane by redistribution of dimethyldichlorosilane with methylchlorosilane an/or methylsilane in the presence of a catalyst comprising a support which is insoluble in the reaction medium and on which tertiary amine groups or quaternary ammonium groups are covalently bonded.

U.S. Pat. Nos. 4,410,669 and 5,130,396 disclose shapeless and spherical polymeric, optionally crosslinked organosiloxane-ammonium compounds having a silica-type backbone, and their use as ion exchangers.

U.S. Pat. No. 5,094,831 describes a process for the dismutation of chlorosilane, in which these are passed in gaseous or liquid form over a catalyst which is shapeless or in the form of spheres and comprises one of four different optionally crosslinked organopolysiloxane compounds essentially carrying an amino or ammonium grouping as the functional group.

SUMMARY OF INVENTION

The object of the present invention is to provide a process for the preparation of dimethylchlorosilane by redistribution of dimethyldichlorosilane with at least one silane having Si-bonded methyl groups, hydrogen atoms and/or chlorine atoms in the presence of a catalyst, in which good yields of dimethylchlorosilane are obtained and in which the redistribution takes place under heterogeneous catalysis, the catalyst can be removed and recovered easily from the reaction mixture, and a continuous procedure is possible.

The invention relates to a process for the preparation of dimethylchlorosilane by redistribution of dimethyldichlorosilane with methylchlorosilane and/or methylsilane in the presence of a catalyst, which comprises using as the catalyst a catalyst which is shapeless or in the form of spheres and is a polymeric, optionally crosslinked organosiloxane-ammonium compound having a silica-type backbone, comprising units of the general formula

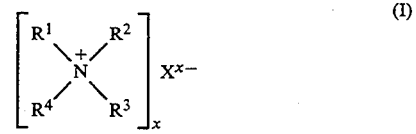

in which $R^1$ and $R^2$ are identical or different and denote a group of the general formula

in which the nitrogen atoms in formula I are bonded to the silicon atoms in formula II via the radical $R^5$ and $R^5$ represents an alkylene group having 1 to 10 carbon atoms, a cycloalkylene group having 5 to 8 carbon atoms or a unit of the general formula

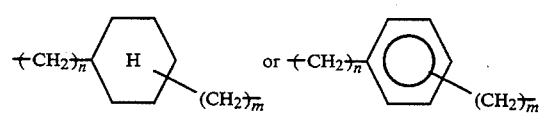

in which n is a number from 1 to 6 and indicates the number of methylene groups on the nitrogen and m is a number from 0 to 6, and in which the free valences of the oxygen atoms bonded to the silicon atom are saturated, as in silicic acid structures, by silicon atoms of further groups of the formula (II) and/or by the metal atoms of one or more of the cross-linking bridge members

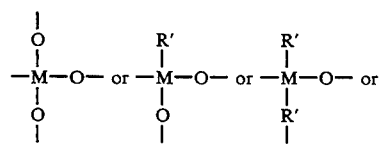

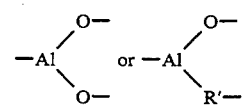

in which M is a silicon, titanium or zirconium atom and R' is a linear or branched alkyl group having 1 to 5 carbon atoms, and the ratio of the silicon atoms from the groups of the general formula (II) to the metal atoms in the bridge members is 1:0 to 1:10, and in which $R^3$ and/or $R^4$ are the same as $R^1$ and $R^2$ or are hydrogen, a linear or branched alkyl group of 1 to 20 carbon atoms, a cycloalkyl group comprising 5 to 8 carbon atoms or the benzyl group and X is an anion having a valency of x of 1 to 3 from the group comprising halide, hydroxide, hypochlorite, sulfate, hydrogen sulfate, nitrite, nitrate, phosphate, dihydrogen phosphate, hydrogen phosphate, carbonate, hydrogen carbonate, chlorate, perchlorate, chromate, dichromate, cyanide, cyanate, thiocyanate, sulfide, hydrogen sulfide, selenide, telluride, borate, metaborate, azide, tetrafluoroborate, tetraphenylborate, hexafluorophosphate, formate, acetate, propionate, oxalate, trifluoroacetate, trichloroacetate and benzoate.

The shapeless catalyst employed in the process according to the invention has a specific surface area of preferably 0.1 to 2000 m$^2$/g and a particle diameter of preferably 0.01 to 3.0 mm. The catalyst in the form of spheres employed in the process according to the invention has a particle diameter of preferably 0.8 to 2.0 mm, a specific surface area of preferably 0 to 1000 m$^2$/g, a specific pore volume of preferably 0 to 5.0 ml/g, a bulk density of preferably 50 to 1000 g/l and a dry matter content per unit volume according to DIN 54 408 of preferably 50 to 750 g/l.

The process according to the invention has the advantage that there is an exchange of Si-bonded chlorine atoms and hydrogen atoms but no exchange of Si-bonded methyl groups takes place during the redistribution.

A compound built up from polymeric units of the formula $[(H_3C)N(CH_2CH_2CH_2SiO_{3/2})^+Cl^-$ is preferably employed as the catalyst in the process according to the invention.

The catalysts employed in the process according to the invention are described in respect of their composition and possible preparation in U.S. Pat. Nos. 4,410,669 and 5,130,396, and the compounds mentioned therein and their preparation are incorporated herein by reference.

Preferably, the methylchlorosilane and/or methylsilane employed in the process according to the invention are prepared by disproportionation of methyldichlorosilane in the presence of a catalyst. Examples of catalysts are tertiary amines, quaternary ammonium salts, such as methyltrioctylammonium chloride and those catalysts comprising a support which is insoluble in the reaction medium and on which tertiary amine or quaternary ammonium groups are covalently bonded, as described in U.S. Pat. No. 4,870,200.

In addition to the main product dimethyldichlorosilane, methyldichlorosilane is obtained during the so-called direct synthesis.

Methylchlorosilane and methylsilane can also be prepared by other processes.

The methylsilane employed in the process according to the invention can be prepared, for example, from methylhydridosiloxanes by the process described in E.L. Zicky, J. Organometal. Chem. 4, 411–412 (1965), or by hydrogenation of methylchlorosilanes with metal hydrides in accordance with W. Noll, Chemie und Technologie der Silicone (Chemistry and Technology of the Silicones), Verlag Chemie, Weinheim, 2nd Edition, pages 76 to 77, 1968.

The process according to the invention is carried out in a heterogeneous phase system.

The adducts of dimethyldichlorosilane and methylchlorosilane and/or methylsilane are preferably employed in gaseous form. However, they can also be employed in liquid form or as a solution in an inert organic solvent such as hexane, toluene, xylene or chlorobenzene.

In the reaction in the gas phase, the solid catalyst is preferably employed in finely divided form in a fixed or fluidized bed or in the form of spheres in a thermostatically controlled tube.

If the catalyst is arranged in a fixed or fluidized bed, gaseous methylchlorosilane and/or methylsilane are passed with gaseous dimethyldichlorosilane through a fixed or fluidized bed comprising the catalyst under a preferred pressure of 0.1 to 15 bar, preferably 1 to 5 bar, and at a preferred temperature of 0° to 300° C., preferably 70° to 150° C., the resulting reaction mixture is condensed and separated by fractional distillation and the dimethylchlorosilane is thus obtained. Preferably, the top product methylsilane, methylchlorosilane or a mixture of methylsilane and methylchlorosilane obtained in a rectifying column during disproportionation of methyldichlorosilane is employed here, the disproportionation being carried out under homogeneous or heterogeneous catalysis in the presence of tertiary amines, quaternary ammonium salts and those catalysts which comprise supports which are insoluble in the reaction medium and on which tertiary amine groups or quaternary ammonium groups are covalently bonded (for example as described in U.S. Pat. No. 4,870,200).

If the catalyst is arranged as shaped pieces in a thermostatically controlled tube, methylchlorosilane and/or methylsilane are introduced, together with dimethyldichlorosilane, under a preferred pressure of 0.1 to 20 bar, preferably 1 to 5 bar, and at a preferred temperature of 0° to 250° C., preferably 70° to 150° C. The resulting reaction mixture is then separated by fractional distillation. Preferably, the top product—methylsilane, methylchlorosilane or a mixture of methylsilane and methylchlorosilane obtained in a rectifying column during disproportionation of methyldichlorosilane—is employed here, the disproportionation being carried out under homogeneous or heterogeneous catalysis in the presence of tertiary amines, quaternary ammonium salts and those catalysts which comprise supports which are insoluble in the reaction medium and on which tertiary amine groups or quaternary ammonium groups are covalently bonded (for example as described in U.S. Pat. No. 4,870,200).

The process according to the invention can be carried out batchwise, semi-continuously or completely continuously. It is preferably carried out completely continuously.

Dimethylchlorosilane is a valuable starting compound for the preparation of functional silanes or siloxanes via hydrosilylation of organic compounds containing an aliphatic double or triple bond and for the preparation of organopolysiloxanes which contain dimethylhydridosilyl groups and which are used in addition, cross-linking silicone rubber compositions.

The methyltrichlorosilane obtained as a by-product, chiefly during disproportionation of methyldichlorosilane, can also be utilized in an economical manner, for example for the preparation of methylsilicone resins and for the preparation of highly disperse silicic acid produced by flame hydrolysis.

Figure 1:
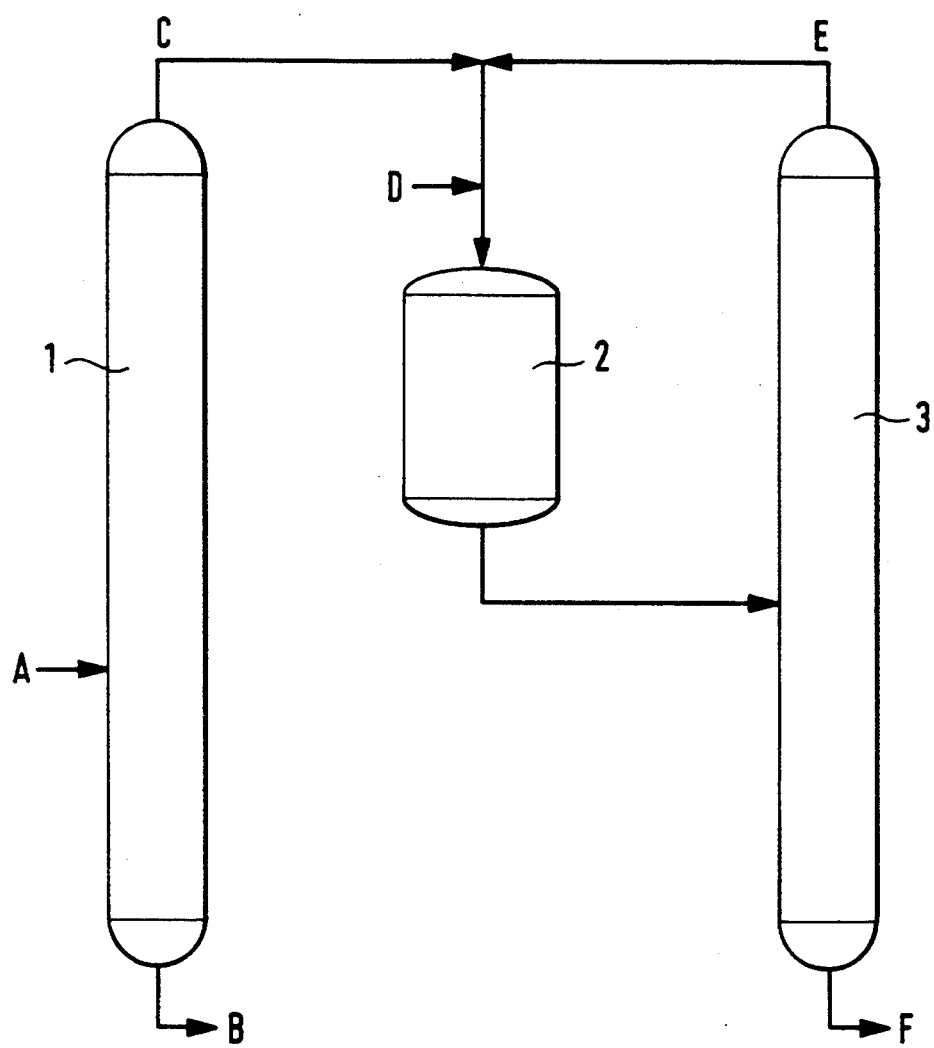
FIG. 1 shows a reactor comprising an adjustable metering pump, a vaporizer, a packed column, a column head with a condenser, a distillation flask, and a device for maintaining a constant pressure.

The following catalysts were used in Examples 1 to 4:

EXAMPLE 1 a. Spherical polymeric organosiloxane-ammonium compound comprising units of the formula $[(H_3C)N(CH_2CH_2CH_2SiO_{3/2})_3]^+Cl^-$ (commercially obtainable under the trade name DELOXAN® AM-PI-1 from Degussa) Particle size: 0.3 to 1.4 mm; Specific surface area (BET) <100 m$^2$/g; Bulk density 700–800 g/l; Dry matter content per unit volume according to DIN 54 408 550–630 g/l.

EXAMPLE 2 b. Spherical polymeric organosiloxane-ammonium compound comprising units of the formula $[(H_3C)N(CH_2CH_2CH_2SiO_{3/2})_3]^+Cl^-$ (commercially obtainable under the trade name DELOXAN ® AM-PI-2 from Degussa) Particle size 1.0 to 1.8 mm.

EXAMPLE 3 c. Spherical polymeric organosiloxane-ammonium compound comprising units of the formula $[(H_3C)N(CH_2CH_2CH_2SiO_{3/2})_3]^+Cl^-$ (commercially obtainable under the trade name DELOXAN ® AM-PI-3 from Degussa) Particle size: 0.6 to 1.2 mm; Specific surface area (BET) 200–300 $m^2/g$; Bulk density 450–550 g/l; Dry matter content per unit volume according to DIN 54 408 250–350 g/l.

EXAMPLE 4 d. Spherical polymeric organosiloxane-ammonium compound comprising units of the formula $[(H_3C)N(CH_2CH_2CH_2SiO_{3/2})_3]^+Cl^-$ (commercially obtainable under the trade name DELOXAN ® AM-PI-3 from Degussa) Particle size: 0.4 to 1.0 mm; Specific surface area (BET) 460–500 $m^2/g$.

The preparation of the catalysts employed in Examples 1 to 4 are described in U.S. Pat. No. 5,130,396, Examples 1 and 2.

The spherical catalysts described above were introduced into a thermostatically controlled tube of 2.4 cm diameter in a bulk height of 15 cm. The amounts and compositions of the silanes passed through in gaseous form were varied and the product compositions emerging from the reaction tube were condensed and analyzed by $^1H$-NMR spectroscopy. The experimental conditions and results are summarized in Table I below.

The $MeSiH_3$ and $MeSiH_3/MeSiH_2Cl$ mixtures used in Examples 1 to 4 were prepared by the process described in U.S. Pat. No. 4,870,200, Example 3.

TABLE 1

| Mixtures | 1 | 2 | 3 | 4 |
|---|---|---|---|---|
| Adducts (mol %) | | | | |
| $MeSiH_3$ | 45.5 | 28.1 | 20.4 | 14.5 |
| $MeSiH_2Cl$ | — | 6.9 | 5.0 | 3.0 |
| $Me_2SiCl_2$ | 55.5 | 65.0 | 75.6 | 82.5 |
| Catalyst temperature (°C.) | 100 | 110 | 120 | 90 |
| Absolute pressure (bar) | 1 | 1 | 1 | 1 |
| Residence time (seconds) | 60 | 60 | 25 | 25 |
| Product composition (mol %) | | | | |
| $MeSiH_3$ | 21.5 | 6.4 | 3.2 | 2.7 |
| $MeSiH_2Cl$ | 20.0 | 16.2 | 10.6 | 7.2 |
| $MeSiHCl_2$ | 3.8 | 11.5 | 10.9 | 7.4 |
| $MeSiCl_3$ | 0.2 | 0.8 | 0.7 | 0.2 |
| $Me_2SiH_2$ | 2.0 | 2.0 | 1.6 | 0.9 |
| $Me_2SiHCl$ | 24.0 | 30.8 | 24.9 | 18.2 |
| $Me_2SiCl_2$ | 29.5 | 32.2 | 49.2 | 63.5 |

EXAMPLE 5 (See FIG. 1):

a. A 50% solution of 3-trimethoxysilyl-propyloctadecyldi-methyl-ammonium chloride in methanol was added to highly disperse silicic acid in the form of spheres of diameter 3–5 mm, KC-Siliperl AF 125 (Kali-Chemie, Hannover, FRG) and the mixture was boiled under toluene reflux for several hours. The solvents were then filtered off and the now functionalized support was dried under vacuum at 100° C.

b. In a V4A steel pilot plant 1, the essential components of which were an adjustable metering pump, a vaporizer, a packed column of 2.5 m overall length and 50 mm internal diameter, a column head with a condenser, a distillation flask of 5 liter capacity and a device for maintaining a constant pressure and emptying the bottom, 825 g/hour of methyldichlorosilane A, which was vaporized continuously in a vaporizer, were fed from a storage vessel by means of a metering pump into the lower part of the column under an absolute pressure of 7 bar.

The methyldichlorosilane, preheated to 95° C., entering column 1 which was filled with catalyst, the preparation of which is described above under (a), disproportionated, with the resulting reaction mixture separating at the same time. The high-boiling methyltrichlorosilane formed (357 g/hour) and the un-reacted methyldichlorosilane (411 g/hour) B collected at the bottom, from which they were discharged into a storage tank. The low-boiling components passed up the column with further reaction. The temperatures in the column were 122° C. at the bottom and 2° C. at the top. The vapor mixture C formed was taken off at the top of the column and passed, together with 600 g/hour of dimethyldichlorosilane D, under 2 bar (absolute) through a tube 2 of 10 cm diameter and 50 cm length, which was thermostatically controlled at 100° C. and half-filled with the catalyst DELOXAN ® AMPI-3, described in Example 3; the gaseous reaction product was condensed by means of a condenser and passed under atmospheric pressure into the middle of a rectifying column 3, which corresponded to the first column in terms of dimensions but was filled with V4A metal coils of 5 mm diameter. The low-boiling components methylsilane, dimethylsilane and methylchlorosilane E were removed at the top of the column and fed to reactor 2. 655 g/hour of a silane mixture F of the following composition were removed continuously from the bottom of column 3: 36.0% by weight of dimethylchlorosilane, 42.6% by weight of demethyldichlorosilane, 19.2% by weight of methyldichlorosilane and 2.3% by weight of methyltrichlorosilane. The mixture was worked up by distillation for separation of the silanes.

EXAMPLES 6

The pilot plant shown in FIG. 1 and described in Example 5 was used. In contrast to Example 5, column 1 was filled with V4A steel Interpak-10 packing and 50 g/hour of methyltrioctylammonium chloride (commercially obtainable under the trade name "Aliquat 336" from Henkel) were metered in 10 cm below the top of the column. Feed A comprised 1 kg/hour of methyldichlorosilane. The bottom discharge B was composed of 30 g/hour of methylchlorosilane, 570 g/hour of methyldichlorosilane, 350 g/hour of methyltrichlorosilane and the amount of homogeneous catalyst methyltrioctylammonium chloride metered in. (The homogeneous catalyst can be recovered again by separating off the silanes, for example by means of a thin film evaporator.) The overall pressure in column 1 was 7 bar (absolute), and the temperature was 125° C. at the bottom and 1° to 5° C. at the top of the column. The top product C was fed, together with 560 g/hour of dimethyldichlorosilane D and the top product from column 3, in gaseous form into the reactor 2 half-filled with the catalyst DELOXAN ® AMPI-3, described in Example 3 (100°, 2 bar). As described in Example 5, the gas mixture emerging was condensed and separated in the rectifying column 3 into a stream of low-boiling components E and a high-boiling silane mixture F (610 g/hour). The silane mixture F (610 g/hour) had the following composition: 32.2% by weight of dimethylchlorosilane, 48.6% by weight of dimethyldichlorosilane, 17.8% by weight of methyldichlorosilane and 1.5% by weight of methyltrichlorosilane. The mixture was worked up by distillation for separation of the silanes.

What is claimed is:

1. A process for preparing dimethylchlorosilane by redistribution of dimethyldichlorosilane with methylchlorosilane and/or methylsilane in the presence of a catalyst, wherein the catalyst is shapeless or in the form of spheres and is a polymeric, optionally crosslinked organosiloxane-ammonium compound having a silica-type backbone, comprising units of the general formula

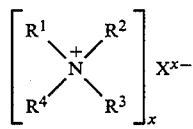
(I)

in which $R^1$ and $R^2$ are identical or different and denote a group of the general formula

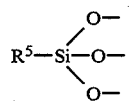
(II)

in which the nitrogen atoms in formula I are bonded to the silicon atoms in formula II via the radical $R^5$ and $R^5$ represents an alkylene group having 1 to 10 carbon atoms, a cycloalkylene group having 5 to 8 carbon atoms or a unit of the general formula

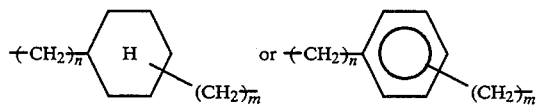

which n is a number from 1 to 6 and indicates the number of methylene groups on the nitrogen and m is a number from 0 to 6, and in which the free valences of the oxygen atoms bonded to the silicon atom are saturated, by silicon atoms of further groups of formula (II) and/or by crosslinking bridge members

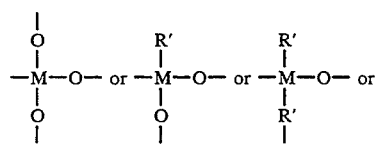

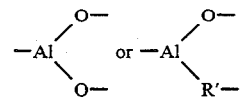

in which M is a silicon, titanium or zirconium atom and R'0 is a linear or branched alkyl group having 1 to 5 carbon atoms, and the ratio of the silicon atoms from the groups of the general formula (II) to the metal atoms in the bridge members is 1:0 to 1:10, and in which $R^3$ and/or $R^4$ are the same as $R^1$ and $R^2$ or are hydrogen, a linear or branched alkyl group of 1 to 20 carbon atoms, a cycloalkyl group comprising 5 to 8 carbon atoms or the benzyl group and X is an anion having a valence of x of 1 to 3 from the group comprising halide, hydroxide, hypochlorite, sulfate, hydrogen sulfate, nitrite, nitrate, phosphate, dihydrogen phosphate, hydrogen phosphate, carbonate, hydrogen carbonate, chlorate, perchlorate, chromate, dichromate, cyanide, cyanate, thiocyanate, sulfide, hydrogen sulfide, selenide, telluride, borate, metaborate, azide, tetrafluoroborate, tetraphenylborate, hexafluorophosphate, formate, acetate, propionate, oxalate, trifluoroacetate, trichloroacetate and benzoate.

2. The process as claimed in claim 1, wherein the shapeless catalyst has a specific surface area of from 0.1 to about 2000 m²/g and a particle diameter of from 0.01 to about 3.0 mm.

3. The process as claimed in claim 1, wherein the catalyst in the form of spheres has a particle diameter of from 0.8 to about 2.0 mm, a specific surface area of from 0 to 1000 m²/g, a specific pore volume of from 0 to about 5.0 ml/g, a bulk density of from 50 to about 1000 g/l, and a dry unit volume of from 50 to about 750 g/l.

4. A process as claimed in claim 1, wherein the dimethyldichlorosilane with methylchlorosilane and/or methylsilane is in a gaseous form.

5. A process as claimed in claim 4, wherein the catalyst is employed in a finely divided form in a fixed or fluidized bed.

6. A process as claimed in claim 1, wherein the catalyst in the form of spheres is contained in a thermostatically controlled tube.

* * * * *

UNITED STATES PATENT AND TRADEMARK OFFICE
CERTIFICATE OF CORRECTION

PATENT NO. : 5,434,286

DATED : July 18, 1995

INVENTOR(S) : Gilbert Geisberger

It is certified that error appears in the above-identified patent and that said Letters Patent is hereby corrected as shown below:

Column 8, line 15, delete "R'O" and insert in lieu of --R'--.

Signed and Sealed this

Seventh Day of November, 1995

Attest:

BRUCE LEHMAN

*Attesting Officer*  *Commissioner of Patents and Trademarks*